(12) United States Patent
Ushio et al.

(10) Patent No.: US 10,241,077 B2
(45) Date of Patent: Mar. 26, 2019

(54) ELECTROCHEMICAL MEASUREMENT DEVICE

(71) Applicant: Panasonic Intellectual Property Management Co., Ltd., Osaka (JP)

(72) Inventors: Hiroshi Ushio, Osaka (JP); Masahiro Yasumi, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 183 days.

(21) Appl. No.: 15/361,533

(22) Filed: Nov. 28, 2016

(65) Prior Publication Data
US 2017/0074821 A1 Mar. 16, 2017

Related U.S. Application Data

(63) Continuation of application No. PCT/JP2016/000068, filed on Jan. 8, 2016.

(30) Foreign Application Priority Data

Jan. 30, 2015 (JP) ................................. 2015-016832

(51) Int. Cl.
*G01N 33/487* (2006.01)
*G01N 27/416* (2006.01)
*C12M 1/34* (2006.01)

(52) U.S. Cl.
CPC ..... *G01N 27/416* (2013.01); *G01N 33/48728* (2013.01); *C12M 1/34* (2013.01)

(58) Field of Classification Search
CPC .. G01N 27/416; G01N 33/48728; C12M 1/34
See application file for complete search history.

(56) References Cited

U.S. PATENT DOCUMENTS

| 6,132,683 A | 10/2000 | Sugihara et al. |
| 2006/0216203 A1 | 9/2006 | Fuller et al. |

FOREIGN PATENT DOCUMENTS

| JP | 2002-523726 | 7/2002 |
| JP | 2008-534965 | 8/2008 |
| WO | 1999/034202 | 7/1999 |

OTHER PUBLICATIONS

International Search Report of PCT application No. PCT/JP2016/000068 dated Mar. 29, 2016.

*Primary Examiner* — J. Christopher Ball
(74) *Attorney, Agent, or Firm* — McDermott Will & Emery LLP (57) ABSTRACT

An electrochemical measurement device includes a chip, a working electrode, a first connection portion, a substrate, a second connection portion, a third connection portion, and an upper plate. The working electrode is disposed on the upper surface of the chip. The first connection portion is disposed on the upper surface of the chip, and is electrically connected to the working electrode. The second connection portion is disposed on the upper surface of the substrate. The third connection portion is disposed on the substrate, is electrically connected to the second connection portion, and is to be electrically connected to an external apparatus. The upper plate is disposed on the upper surfaces of the substrate and chip. The upper plate is provided with a first through hole through which the working electrode is exposed.

19 Claims, 7 Drawing Sheets

FIG. 9

ELECTROCHEMICAL MEASUREMENT DEVICE

BACKGROUND

1. Technical Field

The present disclosure relates to an electrochemical measurement device used for inspecting and analyzing the activity state of a biological piece including a cell or tissue such as a fertilized egg.

2. Background Art

A biological piece including a cell or tissue such as a fertilized egg acts while transporting various materials between its inside and its outside. For example, a fertilized egg takes ambient oxygen into the cell by breathing, and divides in the follicle while consuming the taken oxygen. As methods of measuring the activity state of such a biological piece, methods of electrically measuring a physicochemical state change occurring around the biological piece are known. These methods are used as methods of performing a pharmacological test of a new-drug candidate compound using a model cell and measuring the activity of a fertilized egg.

The conventional measuring apparatus includes a well for storing a biological sample. The well is formed of a lower plate and through holes in an upper plate. In the well, an electrode is formed on the upper surface of the lower plate. An electric contact pad is formed on the lower surface of the lower plate. The electrode is electrically connected to the electric contact pad via a conductive via of the lower plate. Such a conventional measuring apparatus extracts the value of the current that flows through the electrode formed on the lower plate, via the conductive via, from the electric contact pad disposed on the lower surface of the lower plate, and measures the current value.

As a prior technical document relative to the present application, Unexamined Japanese Patent Publication No. 2008-534965 is known, for example

SUMMARY

An electrochemical measurement device of the present disclosure includes a chip, a working electrode, a first connection portion, a substrate, a second connection portion, a third connection portion, and an upper plate. The working electrode is disposed on the upper surface of the chip. The first connection portion is disposed on the upper surface of the chip, and is electrically connected to the working electrode. The second connection portion is disposed on the upper surface of the substrate. The third connection portion is disposed on the substrate, is electrically connected to the second connection portion, and is to be electrically connected to an external apparatus. The upper plate is disposed on the upper surfaces of the substrate and the chip. The upper plate is provided with a first through hole through which the working electrode is exposed.

In the electrochemical measurement device of the present disclosure, the third connection portion to be electrically connected to an external apparatus can be disposed at any position.

DETAILED DESCRIPTION OF PREFERRED EMBODIMENTS

Prior to the descriptions of exemplary embodiments of the present disclosure, a problem of a conventional measuring apparatus is briefly described.

In the conventional measuring apparatus, the electrode is connected to the electric contact pad via the conductive via that is disposed on the lower plate. Therefore, the arrangement of the electric contact pad is limited. Thus, in the conventional measuring apparatus, the electric contact pad cannot be disposed at any position.

Hereinafter, electrochemical measurement devices of the exemplary embodiments of the present disclosure are described in detail with reference to the accompanying drawings. All of the exemplary embodiments described later show preferable specific examples of the present disclosure. Therefore, the numerical values, the shapes, the materials, the components, and the arrangements and connection forms of the components shown in the following exemplary embodiments are examples, and do not intend to limit the present disclosure. Of the components in the following exemplary embodiments, a component that is not described in independent claims showing the highest concept of the present disclosure is described as a non-mandatory (optional) component.

The drawings are schematic diagrams, and are not strictly shown. In the drawings, substantially the same components are denoted with the same reference marks, and duplicate description is omitted or simplified.

In the following description, terms showing directions such as "upper surface", "lower surface", "upward", and "downward" show relative directions that depend on only the relative positional relationship between components of the electrochemical measurement device, and do not show absolute direction such as the vertical direction.

Figure 1:
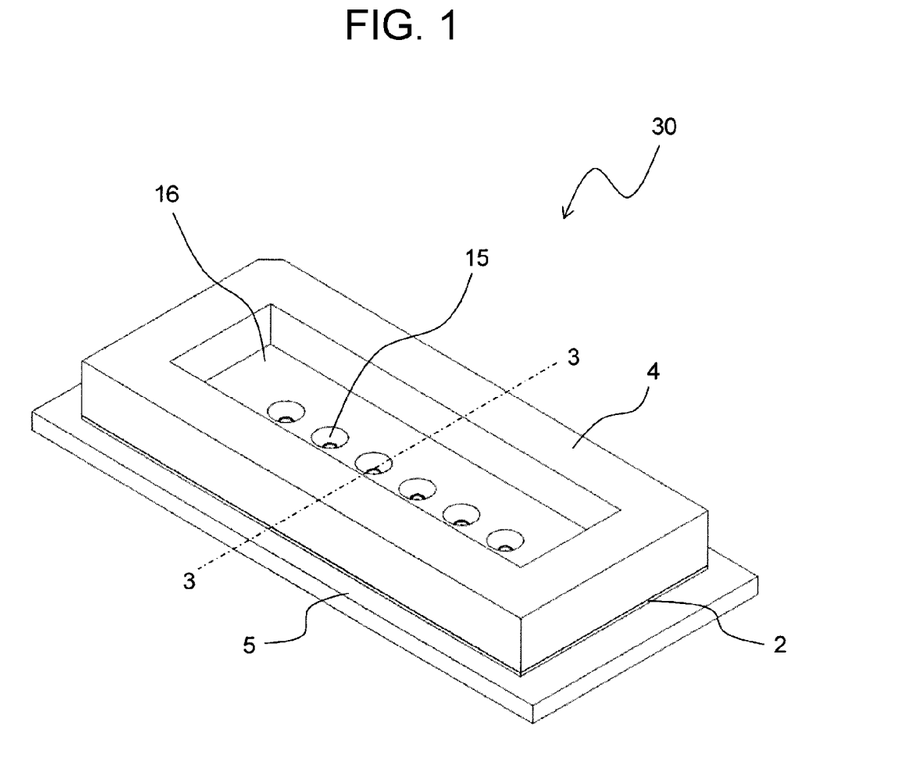
FIG. 1 is a perspective view of an electrochemical measurement device in accordance with an exemplary embodiment.
Figure 2:
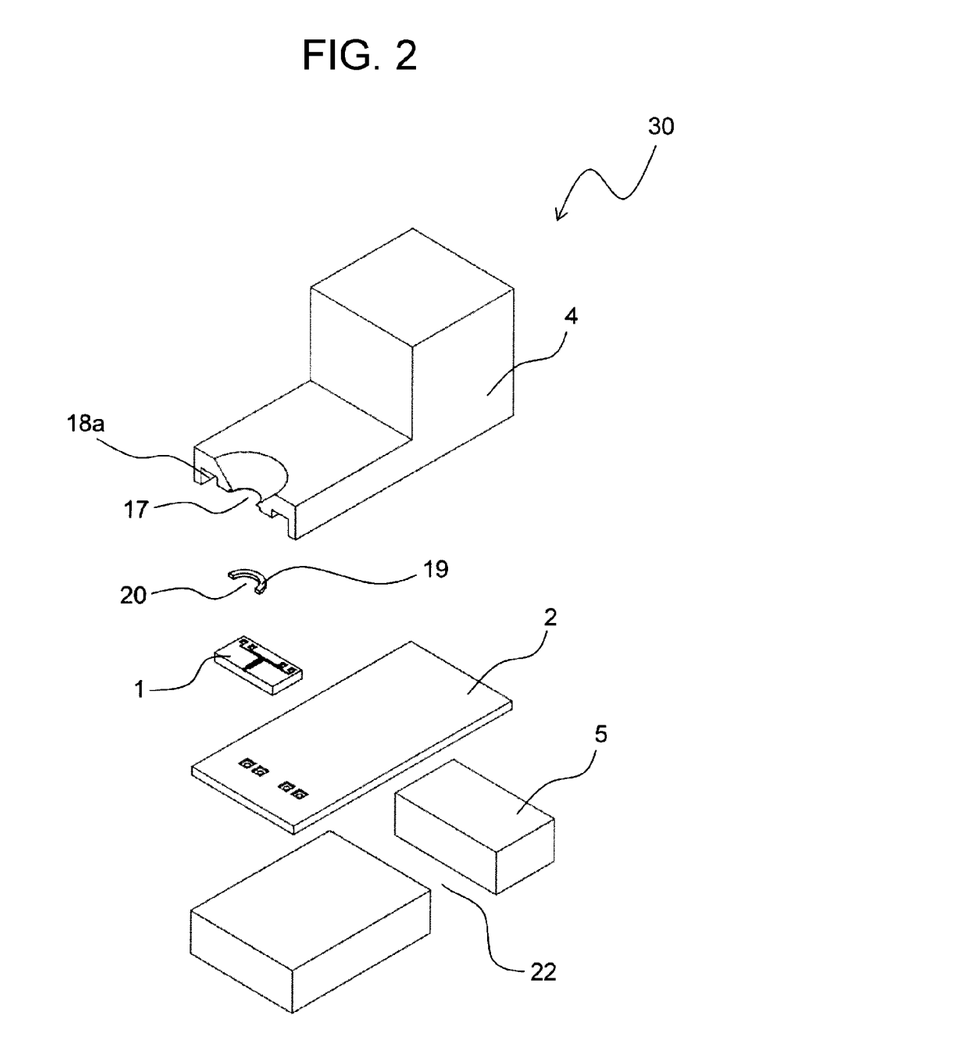
FIG. 2 is an exploded perspective view showing a part of the electrochemical measurement device in accordance with the exemplary embodiment.
Figure 3:
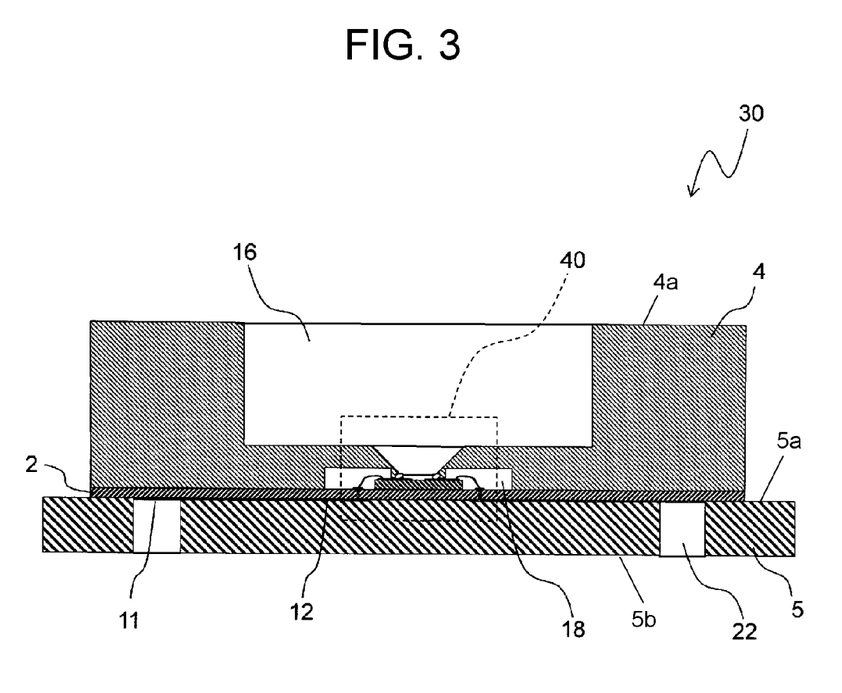
FIG. 3 is a sectional view for schematically showing the electrochemical measurement device in accordance with the exemplary embodiment.
Figure 4:
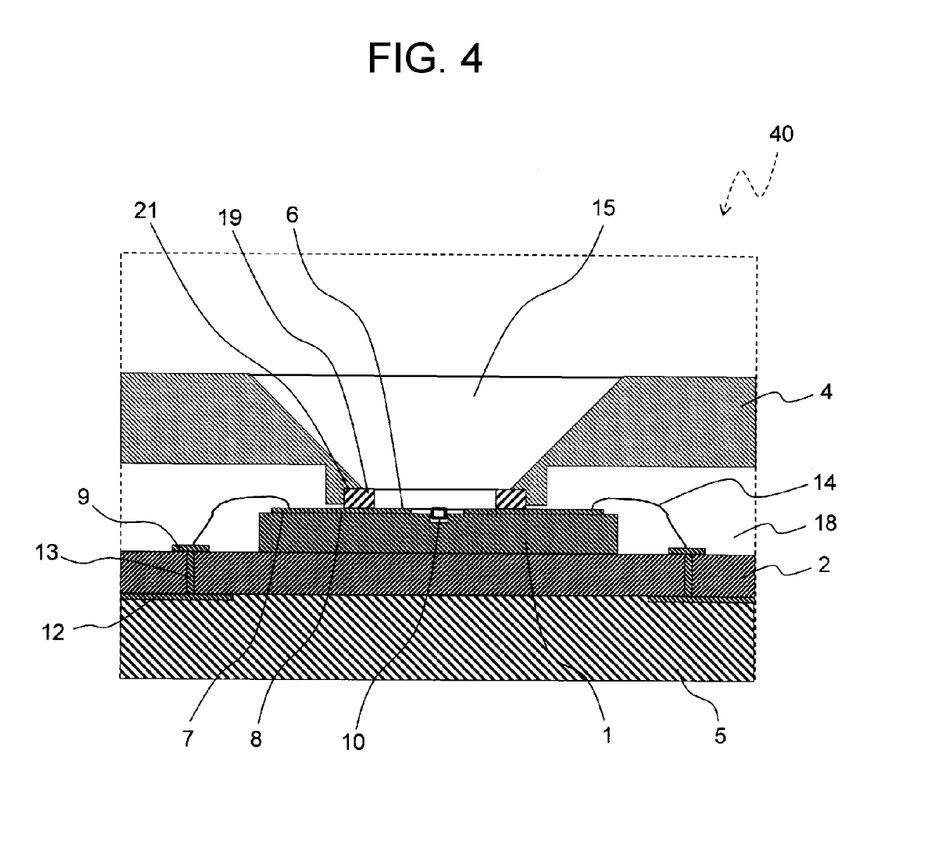
FIG. 4 is an enlarged sectional view of a part of FIG. 3.

FIG. 1 is a perspective view of electrochemical measurement device 30 in accordance with an exemplary embodiment FIG. 2 is an exploded perspective view showing a part of electrochemical measurement device (hereinafter referred to as "device") 30. FIG. 3 is a sectional view for schematically showing the view taken along line 3-3 of device 30 shown in FIG. 1. FIG. 4 is an enlarged sectional view of part 40 shown in FIG. 3.

Device 30 includes chips 1, working electrodes 6, first connection portions 7, substrate 2, second connection portions 9, third connection portions 11, and upper plate 4.

Working electrodes 6 are disposed on the upper surfaces of chips 1, respectively. First connection portions 7 are disposed on the upper surfaces of chips 1, respectively, and are electrically connected to working electrodes 6, respectively. Second connection portions 9 are disposed on the upper surface of substrate 2. Third connection portions 11 are disposed on substrate 2, are electrically connected to second connection portions 9, respectively, and are to be electrically connected to an external apparatus. Upper plate 4 is disposed on the upper surfaces of substrate 2 and chips 1. Upper plate 4 is provided with first through holes 17 through which working electrodes 6 are exposed respectively.

In such a configuration, third connection portions 11 can be disposed at any positions. Therefore, the degree of freedom in design of device 30 is high. In addition, third connection portions 11 are connected to the external apparatus such as a measuring apparatus. Therefore, the positions of third connection portions 11 are determined dependently on the shape of the external apparatus. Since the degree of freedom in design is high, device 30 can be applied to various measuring apparatuses.

Electrochemical measurement device 30 is used for measuring the activity state of biological pieces. The biological pieces are cells or tissues such as fertilized eggs.

As discussed above, device 30 includes chips 1, substrate 2, and upper plate 4. Device 30 further includes lower plate 5 and wells 15 for storing measurement solutions containing biological pieces.

Figure 5:
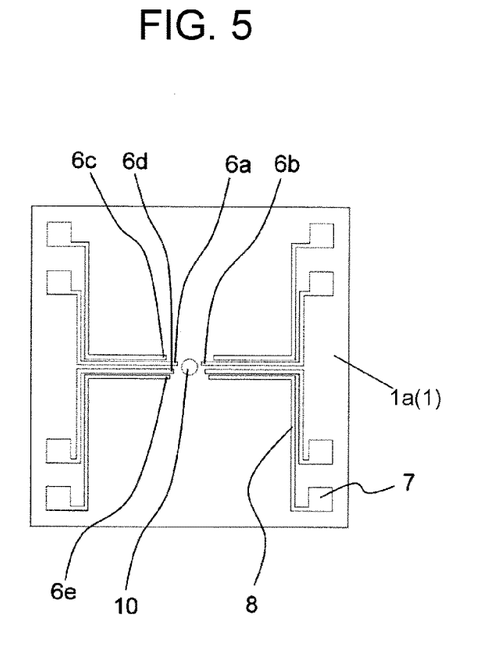
FIG. 5 is a top view for schematically showing a chip in accordance with the exemplary embodiment.

FIG. 5 is a top view for schematically showing chip 1. Chip 1 includes upper surface 1a and a lower surface. On upper surface 1a, working electrodes 6 and first connection portions 7 are formed. Working electrodes 6 are connected to first connection portions 7 via wires 8, respectively. Thus, working electrodes 6 are electrically connected to first connection portions 7, respectively. Each of first connection portion 7 means a part electrically connected to second connection portion 9, of a conductor portion disposed in chip 1. First connection portion 7 may be a part of wire 8.

Chip 1 includes placing portion 10 on which a biological piece is placed. Placing portion 10 is a recess disposed on upper surface 1a of chip 1, for example.

The plurality of working electrodes 6 are disposed on upper surface 1a of chip 1. The plurality of working electrodes 6 are formed around placing portion 10. The plurality of working electrodes 6 include working electrodes 6a to 6e, for example. Working electrode 6a and working electrode 6b are formed at symmetric positions with respect to placing portion 10, for example. By disposing the plurality of working electrodes 6 in that manner, electrochemical variation in the circumference of the biological piece can be two-dimensionally measured. Working electrode 6a is disposed at a position where its distance from placing portion 10 differs from the distances of working electrodes 6c, 6d, and 6e from placing portion 10. By disposing the plurality of working electrodes 6 in that manner, electrochemical variation corresponding to the distance from the biological piece can be measured.

Examples of the material of chip 1 include glass, silicon, ceramic, and resin. Especially, a silicon material can be easily and precisely processed, so that the silicon material is preferable as the material of chip 1. As working electrode 6, a material such as platinum, gold, and silver is used, for example. Working electrodes 6 can be formed on upper surface 1a of chip 1 by fine processing used for a semiconductor process or the like. Therefore, chip 1 can be formed in a fine shape.

First connection portion 7 and wire 8 are made of a conductor such as copper or aluminum. First connection portion 7 and wire 8 may be made of the same material as that of working electrode 6. By making first connection portion 7 and wire 8 using the same material as that of working electrode 6, they can be formed simultaneously with forming of working electrode 6 using the same semiconductor process.

Working electrode 6 may be coated with an insulator so that a part of working electrode 6 is exposed. In this case, the variation in current flowing through the exposed part of working electrode 6 is measured by electrochemical measurement. Preferably, wire 8 interconnecting working electrode 6 and first connection portion 7 is coated with an insulator. In such a configuration, unnecessary contact of the measurement solution with working electrode 6 and wire 8 can be avoided, and electrochemical measurement can be performed accurately. Degradation of working electrode 6 due to the measurement solution or the like can also be suppressed.

Figure 6:
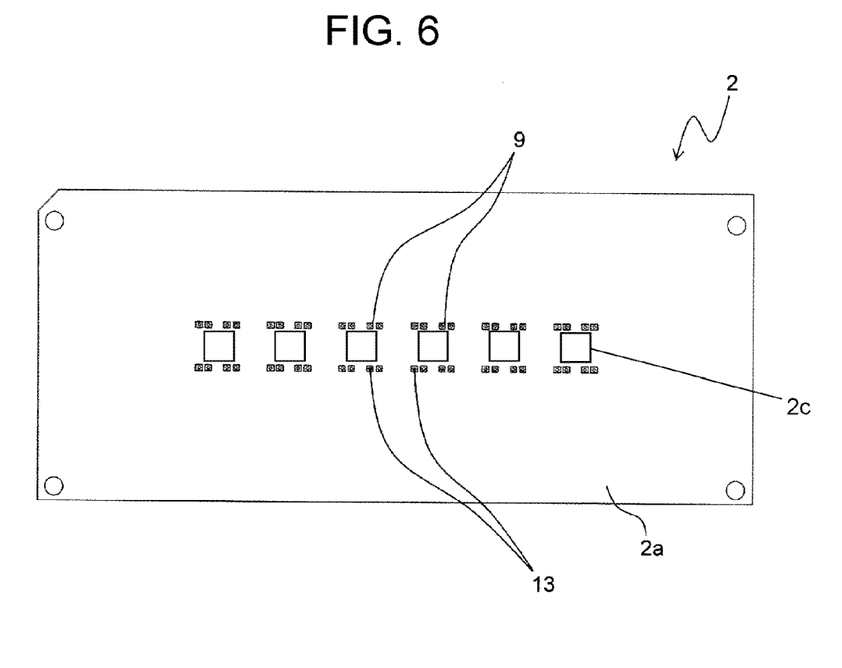
FIG. 6 is a top view for schematically showing a substrate in accordance with the exemplary embodiment.
Figure 7:
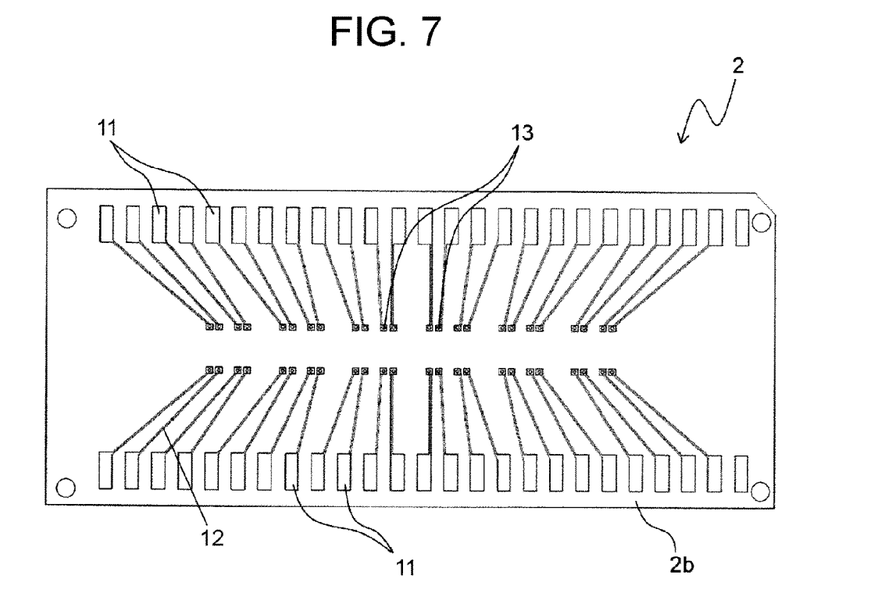
FIG. 7 is a bottom view for schematically showing the substrate in accordance with the exemplary embodiment.

FIG. 6 is a top view for schematically showing substrate 2. FIG. 7 is a bottom view for schematically showing substrate 2. Substrate 2 includes upper surface 2a and lower surface 2b. Chips 1 are disposed on upper surface 2a of substrate 2. Recesses 2c in which chips 1 are disposed, respectively, may be formed on upper surface 2a of substrate 2. In this case, chips 1 are easily positioned on substrate 2. FIG. 4 shows the case that recesses 2c are not disposed. In both cases, chips 1 are fixed to substrate 2 with an adhesive, for example.

Second connection portions 9 electrically connected to first connection portions 7 of chips 1, respectively, are formed on upper surface 2a of substrate 2. Third connection portions 11 are formed on lower surface 2b of substrate 2. Third connection portions 11 are disposed on the periphery of substrate 2. Third connection portions 11 are to be electrically connected to the external apparatus. Wires arranged on another substrate may be disposed between third connection portions 11 and the external apparatus. Third connection portions 11 are used for electrically outputting signals detected by working electrodes 6 to the external apparatus such as a measuring instrument, respectively. As a method of electrically outputting the signals to the measuring instrument, a method of using a contact probe can be employed, for example.

On substrate 2, wires 12 are disposed so as to connect second connection portions 9 to third connection portions 11, respectively. Substrate 2 is provided with through holes 13 penetrating from upper surface 2a to lower surface 2b. A part of each wire 12 is disposed so as to pass through each through hole 13. Thus, second connection portions 9 disposed on upper surface 2a of substrate 2 are electrically connected to third connection portions 11 disposed on lower surface 2b, respectively. Second connection portions 9, third connection portions 11, and wires 12 are made of a conductor such as copper and aluminum.

Each of second connection portions 9 means a part electrically connected to one of first connection portions 7, of a conductor portion disposed on substrate 2. Each of third connection portions 11 means a part electrically connected to a connection terminal or the like of the external apparatus, of a conductor portion disposed on substrate 2. Second connection portion 9 and third connection portion 11 may be parts of each of wires 12.

First connection portions 7, second connection portions 9, and third connection portions 11 are disposed in accordance with the number of working electrodes 6. A signal detected by each working electrode 6 is input to the measuring instrument via first connection portion 7, second connection portion 9, and third connection portion 11 corresponding to each working electrode 6. Therefore, the measuring instrument can individually measure the potential or current of each working electrode 6.

Wire 12 may be coated with an insulator. In such a configuration, breakage of wire 12 can be suppressed during the assembling of device 30.

Examples of substrate 2 include a printed wiring board, a flexible substrate, and a lead frame substrate. Especially, in the case that the printed wiring board is used, wires 12 and through holes 13 can be easily formed, and hence second connection portions 9 can be easily connected to third connection portions 11, respectively. In consideration of the point of view of the assembling ease and cost of device 30, it is preferable to use the printed wiring board.

Next, electric connection between first connection portion 7 and second connection portion 9 is described. First connection portion 7 is disposed as a member different from second connection portion 9. Therefore, during the assembling, the positional relationship between first connection portion 7 and second connection portion 9 sometimes shows that they are separate from each other or they are at positions in height different from each other. Accordingly, as shown in FIG. 4, first connection portion 7 is electrically connected to second connection portion 9 by wire bonding using wire 14, for example. By using wire 14, first connection portion 7 can be certainly connected to second connection portion 9 regardless of the positional relationship between first connection portion 7 and second connection portion 9.

The wire bonding is a method of physically and electrically connecting a connection portion to wire 14 using energy such as heat, ultrasonic wave, or pressure. The material of wire 14 is gold, copper, or aluminum, for example. The diameter of wire 14 is tens of μ meters or hundreds of μ meters, for example. The material and diameter of wire 14 are determined in accordance with the size or material of first connection portion 7 or second connection portion 9. Specifically, wire 14 is an aluminum wire of a diameter of 30 μm, for example. The aluminum wire of a diameter of 30 μm is connected to first connection portion 7 and second connection portion 9 of hundreds of μ meters square by ultrasonic wire bonding. Thus, wire 14 is bonded inexpensively, easily, and accurately. From the point of view of wire bonding work, it is preferable that the distance between first connection portion 7 and second connection portion 9, namely the length of wire 14, is 5 mm or less.

Upper plate 4 is disposed on the upper surfaces of chips 1 and substrate 2. As shown in FIGS. 2 and 3, upper plate 4 is provided with reservoirs 16 for storing the measurement solution on its upper surface, and first through holes 17 formed on the bottom surface of reservoirs 16, respectively. Each of first through holes 17 is formed so as to expose working electrodes 6 and placing portion 10. Well 15 is formed of the inner wall of each first through hole 17 and upper surface 1a of each chip 1. Examples of the material of upper plate 4 include glass, resin, silicon, and ceramic. Especially, it is preferable to employ a resin material from the point of view of the cost.

As shown in FIG. 4, device 30 includes storage portions 18 each of which stores wire 14 between upper plate 4 and substrate 2. Storage portion 18 is a space between upper plate 4 and the upside of first connection portion 7 and second connection portion 9. Upper plate 4 is provided with recesses 18a defining storage portions 18. In each storage portion 18, wire 14 that interconnects first connection portion 7 and second connection portion 9 is stored so that it does not come into contact with upper plate 4. In the case that storage portion 18 is not disposed, there is the possibility that wire 14 comes into contact with upper plate 4 during the assembling and is cut because wire 14 is disposed so as to have a height on substrate 2. When wire 14 is cut, electric connection between first connection portion 7 and second connection portion 9 is eliminated, and hence a connection failure occurs in device 30. Therefore, forming storage portion 18 for wire 14 allows the connection failure in device 30 to be suppressed.

Storage portion 18 may be filled with resin in a state where wire 14 is stored. The filled resin allows wire 14 to be fixed in the resin. Therefore, even if an external impact is applied, the possibility of cutting wire 14 is low, and device 30 can secure stable electric connection.

Annular seal member 19 is disposed between upper plate 4 and each chip 1. Seal member 19 is disposed between working electrodes 6 and first connection portions 7 so that working electrodes 6 is exposed therethrough. Seal member 19 is an elastic body having opening 20 for exposing working electrodes 6. The material of the elastic body is PDMS (polydimethylsiloxane), for example. PDMS has biocompatibility, so that the influence on a biological piece such as a fertilized egg can be reduced.

Upper plate 4 includes seal-member mounting portion 21 on the inner wall of each first through hole 17. Seal-member mounting portion 21 is a groove formed along first through hole 17. Seal member 19 is disposed in seal-member mounting portion 21. Seal-member mounting portion 21 allows seal member 19 to be easily positioned.

Preferably, the height of seal member 19 as an elastic body is greater than that of seal-member mounting portion 21. Preferably, the bottom surface of chip 1 is on the same plane as the lowest surface of upper plate 4. Since seal member 19 is an elastic body, it is compressed in the height direction by the assembling. Therefore, seal member 19 can be firmly sandwiched between upper plate 4 and chip 1. An adhesive layer may be disposed between upper plate 4 and seal member 19. Similarly, an adhesive layer may be disposed between substrate 2 and seal member 19. Furthermore, seal member 19 may be an adhesive or the like.

According to such a configuration, seal member 19 suppresses the measurement solution stored in well 15 from leaking out of well 15. Thus, the contact of the measurement solution with first connection portion 7 and wire 14 can be suppressed. Therefore, device 30 can secure liquid sealability when the measurement solution is filled, and allows accurate electrochemical measurement.

When upper plate 4 and chip 1 can be assembled without a clearance therebetween, the measurement solution can be held in well 15 and hence seal member 19 is not required. However, it is preferable to use seal member 19 to secure the liquid sealability of device 30.

As shown in FIG. 3, lower plate 5 has upper surface 5a and lower surface 5b. Substrate 2 is disposed on upper surface 5a of lower plate 5. Lower plate 5 can increase the strength of device 30. Examples of the material of lower plate 5 include glass, resin, silicon, and ceramic.

Lower plate 5 is provided with second through holes 22 so as to expose third connection portions 11. In such a configuration, third connection portions 11 are disposed inside second through holes 22, respectively. In other words, third connection portions 11 are located above lower surface 5b. Therefore, direct contact of a hand with any of third connection portions 11 can be suppressed. Even if the measurement solution spills and goes around to lower surface 5b, the contact of the spilled measurement solution with any of third connection portions 11 can be suppressed. Third connection portions 11 can be disposed at any positions on substrate 2 in accordance with the shape of the terminal(s) of the external apparatus.

The size of lower plate 5 in the plane direction is greater than that of upper plate 4 in the plane direction. In other words, the edge of lower plate 5 projects to the outside of the edge of the upper plate in the plane direction. In such a configuration, when the measurement solution filled in reservoirs 16 of upper plate 4 spills out, a projection part of upper surface 5a of lower plate 5 receives the spilled measurement solution. The contact of the spilled measurement solution with any of third connection portions 11 can be suppressed. Here, third connection portions 11 are exposed to lower surface 5b through second through holes 22 in lower plate 5, respectively. Also when the size of substrate 2 in the plane direction is greater than that of upper plate 4 in the plane direction, a similar effect is produced. Therefore, it is preferable that at least one of the size of lower plate 5 in the plane direction and the size of substrate 2 in the plane direction is greater than that of upper plate 4 in the plane direction.

Upper plate 4 and lower plate 5 are assembled by screwing, for example. Assembling them by screwing allows each seal member 19 to be compressed between upper plate 4 and respective one of chips 1. Therefore, wells 15 surely sealed against liquid are formed. A measurement solution is held and a biological piece is placed in each well 15 sealed against liquid. By the assembling by screwing, the positions of upper plate 4 and lower plate 5 with respect to substrate 2 can be easily determined.

Upper plate 4, substrate 2, and lower plate 5 are provided with screw holes (not shown). Preferably, screws are attached in the direction in which the screws are inserted into upper plate 4 from lower plate 5. Preferably, the upper surface of upper plate 4 has no hole. In such a configuration, compared with the configuration in which the screws are inserted from upper plate 4, upper surface 4a of upper plate 4 can be a flat surface without unevenness. Furthermore, a problem can be suppressed in which, when the measurement solution spills, infiltration of the spilled measurement solution into a screw hole causes a failure such as short-circuit.

Alternately, substrate 2 may be fixed with upper plate 4 and lower plate 5 with an adhesive therebetween.

Lower plate 5 is not always required. When lower plate 5 is not used, the assembling process of device 30 can be simplified, and the height of device 30 can be reduced.

Figure 8:
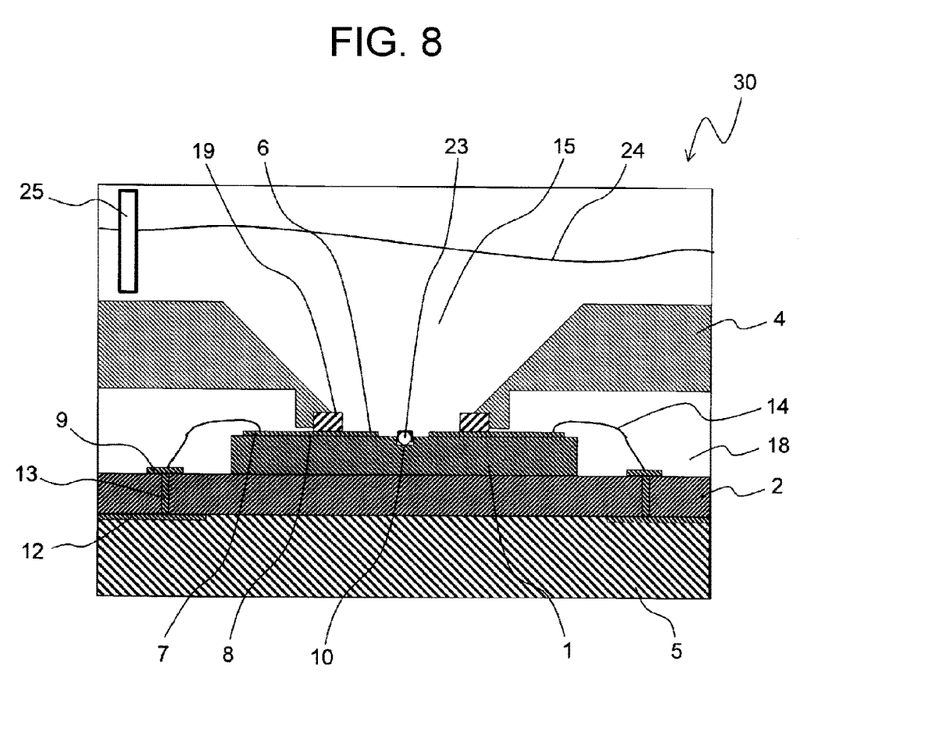
FIG. 8 is a sectional view for illustrating an operation of the electrochemical measurement device in accordance with the exemplary embodiment.

Next, the operation of device 30 is described. FIG. 8 is a sectional view showing device 30 in use.

Biological piece 23 is a fertilized egg, for example. The fertilized egg divides in the follicle while consuming the ambient oxygen. Device 30 measures, with working electrodes 6, the dissolved oxygen content in the measurement solution. When the fertilized egg exists in the measurement solution, the dissolved oxygen content around the fertilized egg can be measured using device 30. The dissolved oxygen content around the fertilized egg is correlated with the oxygen content consumed due to the activity of the fertilized egg. Therefore, the activity state of the oxygen consumption by the fertilized egg can be checked. Hereinafter, the fertilized egg is described as biological piece 23.

Measurement solution 24 including biological piece 23 is injected into well 15. Then, biological piece 23 is placed on placing portion 10 disposed on chip 1.

Next, reference electrode 25 is disposed so as to be in contact with measurement solution 24. As the material of reference electrode 25, Ag/AgCl, Pt, or Au is used.

Then, using the plurality of working electrodes 6 and one reference electrode 25, the current flowing between each of working electrodes 6 and reference electrode 25 is measured. On the basis of the measured current values, the dissolved oxygen content in measurement solution 24 can be calculated. Reference electrode 25 has two functions as a counter electrode and a reference electrode. However, the counter electrode and the reference electrode may be disposed as separate electrodes.

Figure 9:
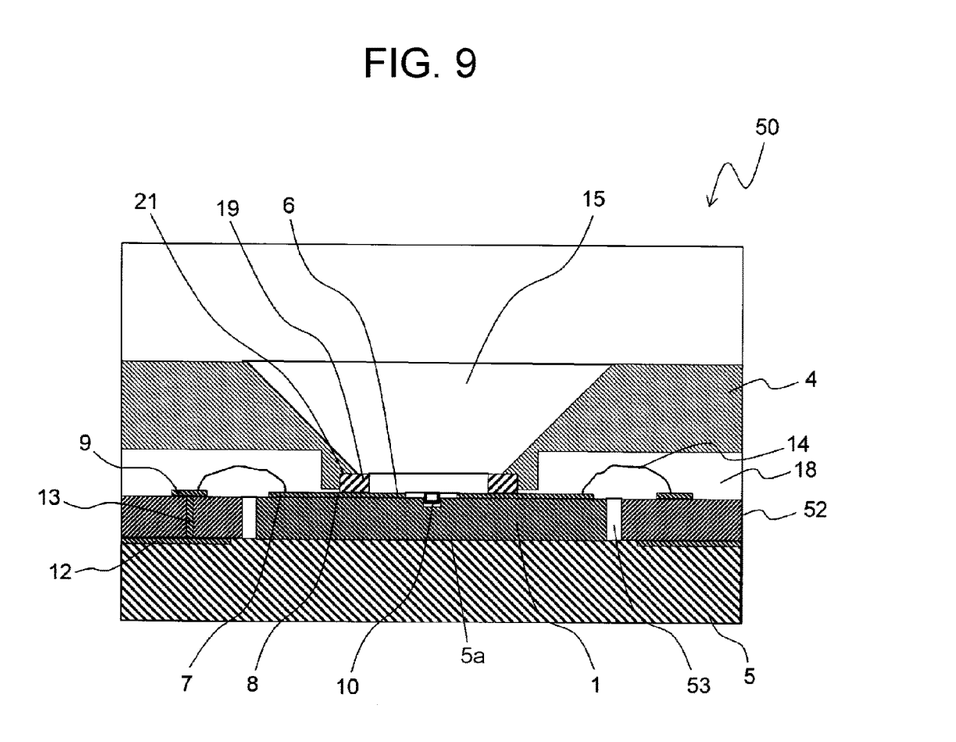
FIG. 9 is a sectional view for schematically showing a modified example of the electrochemical measurement device in accordance with the exemplary embodiment.

Hereinafter, electrochemical measurement device (hereinafter referred to as "device") 50, which is a modified example of the present exemplary embodiment, is described with reference to a drawing. The same components as those of device 30 are denoted with the same reference marks, and the description of them is omitted, and the difference is described in detail.

FIG. 9 is a sectional view of device 50. Device 50 differs from device 30 shown in FIG. 4 in that chip 1 and substrate 52 are disposed on upper surface 5a of lower plate 5.

In device 50, chip 1 and substrate 52 are disposed so as to be in contact with upper surface 5a of lower plate 5. Substrate 52 is disposed around chips 1. For example, substrate 52 includes third through holes 53 each of which has a size allowing chip 1 to be stored therein. Chip 1 is disposed in third through hole 53. In such a configuration, chip 1 can be positioned using third through hole 53, so that device 50 can be easily assembled.

The thickness of chip 1 may be the same as that of substrate 52, or may be different from it. When the thickness of chip 1 is the same as that of substrate 52, the structure is simpler and the assembling is easier. For example, in a process of connecting first connection portions 7 to second connection portions 9 via wires 14, respectively, wires 14 can be easily bonded when the height of chip 1 is the same as that of substrate 52.

Although not shown, also in device 50 similarly to device 30, it is preferable that at least one of the size of lower plate 5 in the plane direction and the size of substrate 52 in the plane direction is greater than that of upper plate 4 in the plane direction. Similarly to FIG. 3, lower plate 5 preferably includes second through holes 22 through which third connection portions 11 are exposed.

Preferably, the materials used for chips 1, upper plate 4, seal members 19, and working electrodes 6 are made of materials that do not affect a biological piece.

In devices 30 and 50, the number of working electrodes 6 and the number of the connection portions can be optionally determined in accordance with an object to be measured or measuring method. Each number may be one, or two or more. The shapes of working electrodes 6, wires 8, and first connection portions 7 that are disposed on the upper surface of chip 1, and the shapes of wires 12, second connection portions 9, and third connection portions 11 that are disposed on substrate 2 can be optionally determined.

Electrochemical measurement devices based on one or a plurality of aspects are described on the basis of the exemplary embodiments. However, the present disclosure is not limited to the exemplary embodiments. The following forms may be included in the range of the one or the plurality of aspects as long as they do not deviate from the scope of the present disclosure. The forms are a form obtained by applying various modifications conceived by persons skilled in the art to the present exemplary embodiment, and a form obtained by combining components in different exemplary embodiments.

The electrochemical measurement device of the present disclosure is useful for inspecting and analyzing the activity state of a biological piece.

What is claimed is:

1. An electrochemical measurement device comprising:
   a chip;
   a working electrode disposed on an upper surface of the chip;
   a first connection portion disposed on the upper surface of the chip, and electrically connected to the working electrode;
   a substrate;
   a second connection portion disposed on an upper surface of the substrate;
   a third connection portion disposed on a lower surface opposite to the upper surface of the substrate, electrically connected to the second connection portion, and to be electrically connected to an external apparatus; and
   an upper plate disposed on the upper surface of the substrate and on the upper surface of the chip,
   wherein the upper plate is provided with a first through hole through which the working electrode is exposed.

2. The electrochemical measurement device according to claim 1, wherein the chip is disposed on the upper surface of the substrate.

3. The electrochemical measurement device according to claim 2, wherein the upper surface of the substrate is provided with a recess in which the chip is disposed.

4. The electrochemical measurement device according to claim 2, further comprising a lower plate,
   wherein the substrate is disposed on an upper surface of the lower plate.

5. The electrochemical measurement device according to claim 4, wherein at least one of a size in a plane direction of the lower plate and a size in a plane direction of the substrate is greater than a size in a plane direction of the upper plate.

6. The electrochemical measurement device according to claim 4, wherein the lower plate is provided with a second through hole through which the third connection portion is exposed.

7. The electrochemical measurement device according to claim 1, further comprising a lower plate,
   wherein the chip and the substrate are disposed on an upper surface of the lower plate, and
   the substrate is disposed around the chip.

8. The electrochemical measurement device according to claim 7, wherein the substrate is provided with a second through hole in which the chip is disposed.

9. The electrochemical measurement device according to claim 7, wherein at least one of a size in a plane direction of the lower plate and a size in a plane direction of the substrate is greater than a size in a plane direction of the upper plate.

10. The electrochemical measurement device according to claim 7, wherein the lower plate is provided with a second through hole through which the third connection portion is exposed.

11. The electrochemical measurement device according to claim 1, further comprising a wire electrically connecting the first connection portion to the second connection portion,
    wherein the upper plate includes a storage portion facing the substrate, and accommodating the wire therein.

12. The electrochemical measurement device according to claim 11, wherein the wire is made of one of gold, copper, and aluminum.

13. The electrochemical measurement device according to claim 1, further comprising a seal member disposed between the chip and the upper plate and positioned between the working electrode and the first connection portion.

14. The electrochemical measurement device according to claim 13, wherein the seal member is made of an elastic body or an adhesive.

15. The electrochemical measurement device according to claim 1, further comprising a seal member disposed between the chip and the upper plate,
    wherein the seal member is provided with an opening through which the working electrode is exposed.

16. The electrochemical measurement device according to claim 15, wherein the seal member is made of an elastic body or an adhesive.

17. The electrochemical measurement device according to claim 1, wherein the substrate is one of a printed wiring board, a flexible substrate, and a lead frame substrate.

18. An electrochemical measurement device comprising:
    a chip;
    a working electrode disposed on an upper surface of the chip;
    a first connection portion disposed on the upper surface of the chip, and electrically connected to the working electrode;
    a substrate;
    a second connection portion disposed on an upper surface of the substrate;
    a third connection portion disposed on the substrate, electrically connected to the second connection portion, and to be electrically connected to an external apparatus;
    an upper plate disposed on the upper surface of the substrate and on the upper surface of the chip, and
    a wire electrically connected to the first connection portion and the second connection portion
    wherein the upper plate is provided with a first through hole through which the working electrode is exposed, and
    the upper plate includes a storage portion facing the substrate, and accommodating the wire therein.

19. The electrochemical measurement device according to claim 18, wherein the wire is made of one of gold, copper, and aluminum.

* * * * *